(12) United States Patent
Dempsey

(10) Patent No.: US 12,429,532 B2
(45) Date of Patent: *Sep. 30, 2025

(54) MAGNETIC RESONANCE IMAGING

(71) Applicant: ViewRay Systems, Inc., Denver, CO (US)

(72) Inventor: James F. Dempsey, Atherton, CA (US)

(73) Assignee: ViewRay Systems, Inc., Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 18/540,666

(22) Filed: Dec. 14, 2023

(65) Prior Publication Data

US 2024/0310457 A1    Sep. 19, 2024

Related U.S. Application Data

(63) Continuation of application No. 17/848,277, filed on Jun. 23, 2022, now Pat. No. 11,892,523, which is a continuation of application No. 15/630,890, filed on Jun. 22, 2017, now Pat. No. 11,378,629.

(60) Provisional application No. 62/353,538, filed on Jun. 22, 2016.

(51) Int. Cl.
| | | |
|---|---|---|
| *G01R 33/00* | (2006.01) | |
| *A61B 5/055* | (2006.01) | |
| *A61N 5/10* | (2006.01) | |
| *G01R 33/28* | (2006.01) | |
| *G01R 33/38* | (2006.01) | |
| *G01R 33/381* | (2006.01) | |
| *G01R 33/3815* | (2006.01) | |
| *G01R 33/385* | (2006.01) | |
| *G01R 33/48* | (2006.01) | |
| *G01R 33/483* | (2006.01) | |
| *G01R 33/563* | (2006.01) | |
| *G01R 33/565* | (2006.01) | |

(52) U.S. Cl.
CPC .......... *G01R 33/0023* (2013.01); *A61B 5/055* (2013.01); *A61N 5/1049* (2013.01); *G01R 33/0017* (2013.01); *G01R 33/287* (2013.01); *G01R 33/3815* (2013.01); *G01R 33/385* (2013.01); *G01R 33/48* (2013.01); *A61N 2005/1055* (2013.01); *G01R 33/3806* (2013.01); *G01R 33/381* (2013.01); *G01R 33/4808* (2013.01); *G01R 33/4835* (2013.01); *G01R 33/56325* (2013.01); *G01R 33/56527* (2013.01); *G01R 33/56536* (2013.01)

(58) Field of Classification Search
CPC ............ G01R 33/0023; G01R 33/0017; G01R 33/287; G01R 33/385; A61B 5/055
See application file for complete search history.

(56) References Cited

U.S. PATENT DOCUMENTS

| | | | |
|---|---|---|---|
| 11,378,629 B2 * | 7/2022 | Dempsey ........... | G01R 33/0017 |
| 11,768,257 B2 * | 9/2023 | Dempsey ............... | G01R 33/48 |
| | | | 324/318 |
| 11,892,523 B2 * | 2/2024 | Dempsey ............... | A61B 5/055 |

* cited by examiner

*Primary Examiner* — Reena Aurora
(74) *Attorney, Agent, or Firm* — Davis Graham & Stubbs LLP

(57) ABSTRACT

Improved magnetic resonance imaging systems, methods and software are described including a low field strength main magnet, a gradient coil assembly, an RF coil system, and a control system configured for the acquisition and processing of magnetic resonance imaging data from a patient while utilizing a sparse sampling imaging technique.

8 Claims, 3 Drawing Sheets

MAGNETIC RESONANCE IMAGING

CROSS-REFERENCE TO RELATED APPLICATION

This application is a continuation of U.S. patent application Ser. No. 17/848,277 filed Jun. 23, 2022 entitled "MAGNETIC RESONANCE IMAGING," which is a continuation of U.S. patent application Ser. No. 15/630,890 (now U.S. Pat. No. 11,378,629), filed Jun. 22, 2017, entitled "MAGNETIC RESONANCE IMAGING," which claims the benefit of priority under 35 U.S.C. 119 of U.S. Provisional Application No. 62/353,538, filed Jun. 22, 2016, entitled "MAGNETIC RESONANCE IMAGING," the disclosures of each are incorporated herein by reference in their entirety.

TECHNICAL FIELD

The subject matter described herein relates to systems, methods and computer software for magnetic resonance imaging and various diagnostic and interventional applications associated therewith.

BACKGROUND

Magnetic resonance imaging (MRI), or nuclear magnetic resonance imaging, is a noninvasive imaging technique that uses the interaction between radio frequency pulses, a strong magnetic field (modified with weak gradient fields applied across it to localize and encode or decode phases and frequencies) and body tissue to obtain projections, spectral signals, and images of planes or volumes from within a patient's body. Magnetic resonance imaging is particularly helpful in the imaging of soft tissues and may be used for the diagnosis of disease. Real-time or cine MRI may be used for the diagnosis of medical conditions requiring the imaging of moving structures within a patient. Real-time MRI may also be used in conjunction with interventional procedures, such as radiation therapy or image guided surgery, and also in planning for such procedures.

SUMMARY

Magnetic resonance imaging systems, methods and software are disclosed. Some implementations may be used in conjunction with a main magnet having a low field strength, a gradient coil assembly, an RF coil system, and a control system configured for the acquisition and processing of magnetic resonance imaging data from a human patient while utilizing a sparse sampling imaging technique without parallel imaging.

In some variations, the field strength of the main magnet is less than 1.0 Tesla and in others the field strength is approximately 0.35 T.

In some implementations, the control system of the MRI may be configured to utilize low gradient field strengths (e.g., below 20 mT/m), to utilize large flip angles (e.g., greater than 40 degrees), to utilize RF bandwidths to maintain chemical shift and magnetic susceptibility artifacts to less than one millimeter (e.g., RF bandwidths less than 1800 Hz), to utilize a gradient slew rate above 75 mT/m/ms, and/or to employ pulse sequences that do not require dephasing or spoiler pulses. In some implementations, the RF coil system may not include a surface coil.

The control system of the magnetic resonance imaging system may also be configured to produce cine MRI (e.g., of least 4 frames per second).

In another implementation, the magnetic resonance imaging system may be integrated with a radiation therapy device for radiation treatment of a human patient and the control system may be further configured to utilize cine MRI to track the locations of tissues in the human patient. The radiation therapy device may be a linear accelerator having an energy in the range of, for example, 4-6 MV. The radiation therapy device may also be a proton therapy system, heavy ion therapy system, or a radioisotope therapy system.

The magnetic resonance imaging system may also comprise a split/open bore magnet and be configured to allow for surgical intervention in the gap of the split magnet, for example, with a robotic surgical device integrated into the system. Similarly, the gradient coil assembly may be a split gradient coil assembly. The main magnet may be a superconducting magnet, a non-superconducting magnet, or a resistive magnet. The main magnet may be powered by a battery system.

Implementations of the current subject matter can include, but are not limited to, methods consistent with the descriptions provided herein as well as articles and computer program products that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

The present disclosure describes systems, methods and computer software allowing for, among other things, high-quality magnetic resonance imaging with limited magnetic susceptibility distortions and chemical shift artifacts resulting in submillimeter spatial accuracy, high frame rate cine capability with an appropriate specific absorption rate (SAR), and the ability to support real-time 2-D and volumetric MRI-guided diagnostic and interventional applications.

Figure 1:
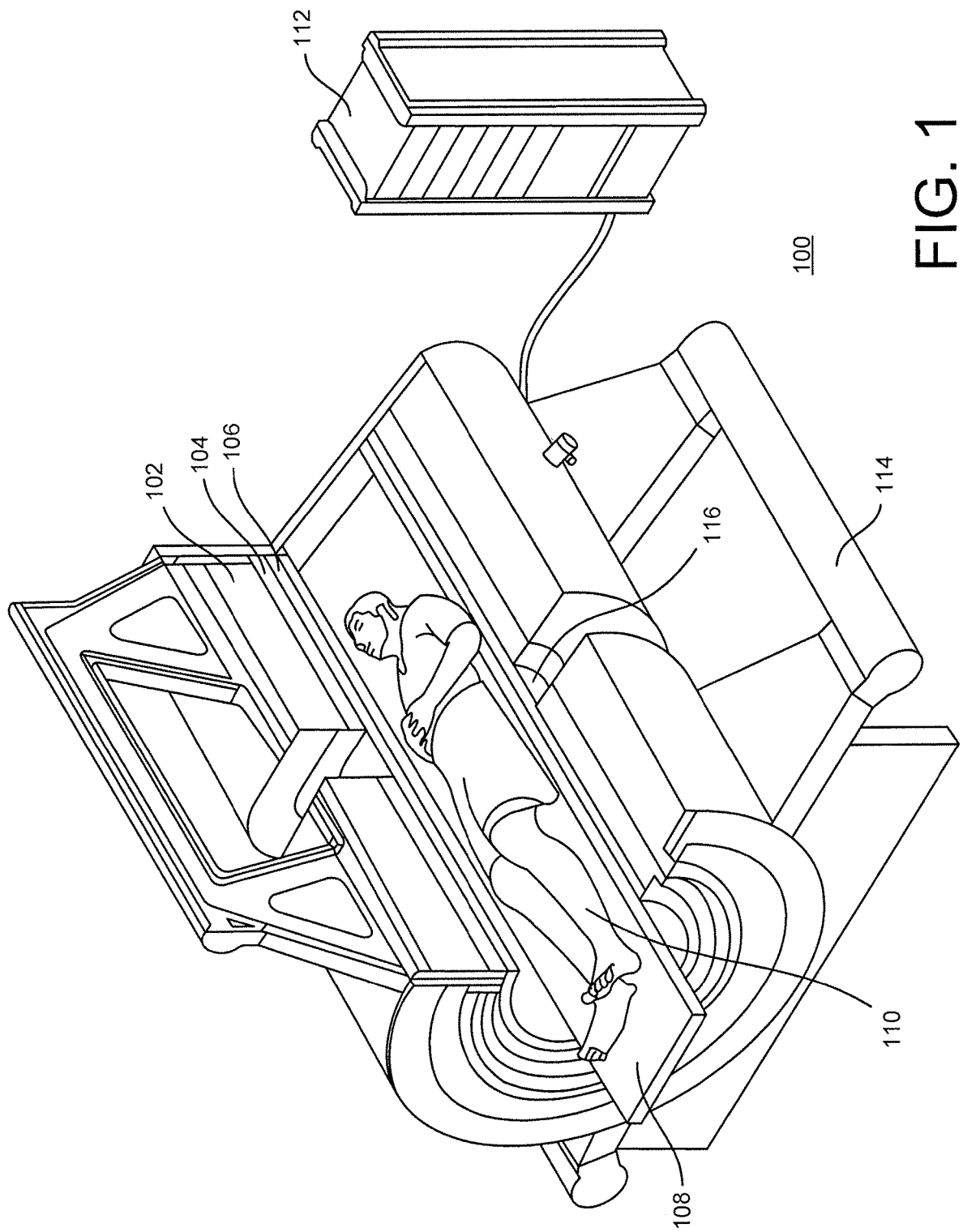
FIG. 1 is a diagram illustrating a simplified perspective view of an exemplary magnetic resonance imaging system in accordance with certain aspects of the present disclosure.

FIG. 1 illustrates one implementation of a magnetic resonance imaging system (MRI) 100 consistent with certain aspects of the present disclosure. In FIG. 1, the MRI 100 includes a main magnet 102, a gradient coil assembly 104 and an RF coil system 106. Within MRI 100 is a patient couch 108 on which a human patient 110 may lie. MRI 100 also includes a control system 112, discussed in detail below.

The main magnet 102 of MRI 100 may be a cylindrical split or open bore magnet separated by buttresses 114, with a gap 116 as shown in FIG. 1, a closed-bore cylindrical configuration, a C-shaped configuration, a dipolar magnet, or the like. Main magnet 102 may be comprised of a number of magnet types, including electromagnets, permanent magnets, superconducting magnets, or combinations thereof. For example, one combination or "hybrid" magnet may include permanent magnets and electromagnets. Main magnet 102 may be configured for any commonly used field strength, but is preferably configured for a low field strength. When the term low field strength is used herein, it refers to a field strength of less than 1.0 Tesla. In particular implementations of the present disclosure, the field strength of main magnet 102 may be configured to be in the range of 0.1 to 0.5 Tesla, or configured to be approximately 0.35 Tesla. The system may be designed to use resistive or permanent magnets, or a combination thereof, for example, when the field strength of the main magnet is less than approximately 0.2 Tesla. In one implementation, a system utilizing resistive magnet(s) may be powered by a direct-current battery system, for example, a lithium ion system such as, or similar to, a Tesla Powerwall.

Gradient coil assembly 104 contains the coils necessary to add small varying magnetic fields on top of main magnet 102's field to allow for spatial encoding of the imaging data. Gradient coil assembly 104 may be a continuous cylindrical assembly, a split gradient coil assembly as shown in FIG. 1, or other designs as may be necessary for the particular MRI configuration utilized.

RF coil system 106 is responsible for exciting the spins of hydrogen protons within patient 110 and for receiving subsequent signals emitted from patient 110. RF coil system 106 thus includes an RF transmitter portion and an RF receive portion. The implementation in FIG. 1 includes a singular body coil performing both the RF transmit and RF functionalities. RF coil system 106 may alternatively divide transmit and receive functionalities between a body coil and a surface coil, or may provide both transmit and receive functionalities within a surface coil. The RF coil system 106 depicted in the implementation of FIG. 1 has a continuous cylindrical form but could also be designed in a split manner, so that gap 116 would be open from the patient to the outer edge of main magnet 102.

Control system 112 is configured for the acquisition and processing of magnetic resonance imaging data from patient 110, including image reconstruction. Control system 112 may contain numerous subsystems, for example, those which control operation of the gradient coil assembly 104, the RF coil system 106, portions of those systems themselves, and those that process data received from RF coil system 106 and perform image reconstruction.

In one advantageous implementation, control system 112 is configured to utilize a sparse sampling imaging technique without parallel imaging. When the term sparse sampling imaging technique is used herein it refers to image acquisition and reconstruction techniques where only a portion of frequency space is measured (for the purposes of the present disclosure, 50% or less of the frequency information used to reconstruct an image using standard back-projection methods), and the image reconstruction is performed by optimization of the reconstructed image to be consistent with a priori knowledge of the imaged subject while also generally satisfying consistency between the frequency information of the reconstructed image and the measured frequency information. Sparse sampling imaging techniques thus include techniques such as compressed sensing and the volumetric imaging technique disclosed in U.S. Patent Application No. 62/353,530, filed concurrently herewith and assigned to ViewRay Technologies, Inc.

Parallel imaging techniques are commonly used in magnetic resonance imaging, especially with cine MRI, to shorten the time required for data acquisition. Parallel imaging methods use knowledge of the spatial distribution of signals received by multiple RF detectors (such as a surface coil having an array of these "elements") to replace some of the time-consuming phase-encoding steps in the MRI process. In this manner, signal is received from multiple coil elements "in parallel," and the sampling of fewer portions in k-space along readout trajectories (i.e., fewer phase encodings) is compensated for by the duplicity of data from all coil elements.

However, certain implementations of the present disclosure contemplate data acquisition and processing without utilizing parallel imaging techniques. In such cases where the present disclosure refers to magnetic resonance data acquisition and processing "without parallel imaging" it contemplates systems, methods and computer software designed to incorporate a small amount parallel imaging (perhaps in an attempt to avoid infringement), but not enough to create a perceptively significant increase in signal-to-noise ratio, all other things being constant.

In some advantageous implementations, the MRI and control system 112 may be configured to utilize low gradient field strengths, for example below 20 mT/m or, in other cases, below 12 mT/m. In addition, some advantageous implementations may utilize a relatively high gradient slew rate or rise time, such as a slew rate above 75 mT/m/ms. Control system 112 may also be advantageously configured to utilize large flip angles, for example, greater than 40 degrees. In addition, control system 112 may be advantageously configured to employ pulse sequences that do not require dephasing pulses (it is contemplated that such pulse sequences have no dephasing pulses, or have only a small number of dephasing or spoiling pulses such that there is no significant increase in data acquisition time from the standpoint of patient throughput).

In some implementations, control system 112 may be configured to utilize RF bandwidths to maintain chemical shift and magnetic susceptibility artifacts below one millimeter or even below one half of a millimeter. As an example, control system 112 may be configured for an RF bandwidth less than 1800 Hz. An evaluation of potential worst-case artifacts due to magnetic susceptibility and chemical shift can be evaluated. For example, for a worst case of, e.g., 8 ppm perturbation observed in human susceptibility assessments, formula [1] below can be used to estimate magnetic susceptibility artifacts.

$$\delta_{ms}[mm] = mag.suscept.[ppm] \times \frac{B_o[T]}{G_e[T/mm]} \quad [1]$$

Here $\delta_{ms}$[mm] is the spatial distortion in millimeters due to magnetic susceptibility artifacts due to a magnetic susceptibility induced magnetic field change, mag. suscept. [ppm] in parts per million of the main magnetic field strength, $B_o$[T], in Tesla, and where $G_e$[T/mm] is the gradient encoding strength in Tesla per millimeter.

And, formula [2] below may be used to estimate displacements due to chemical shift.

$$\delta_{cs}[mm] = 3.5 \text{ [ppm]} \times \text{PixelSize [mm]} \times \frac{f_{B_o}[Hz]}{BW[Hz/pixel]} \quad [2]$$

Here $\delta_{cs}$[mm] is the spatial distortion in millimeters due to chemical shift artifacts, where 3.5 [ppm] is the relative parts per million difference in the Larmour frequency for Hydrogen bound to Oxygen (H—O) versus Carbon (C—H) for a Pixel or Voxel size, PixelSize, in millimeters, and $f_{B_o}$ is the Larmour frequency for Hydrogen in water and BW[Hz/pixel] is the frequency bandwidth for a pixel or voxel in Hertz per pixel or voxel.

A worst-case distortion can be taken as the sum of these two distortions plus any residual distortions due to uncorrected gradient field nonlinearities.

In one particular implementation of the magnetic resonance imaging system 100 of the present disclosure, the main magnet 102 field strength is approximately 0.35 Tesla and control system 112 is configured to utilize gradient field strengths below 12 mT/m, a gradient slew rate above 75 mT/m/ms, flip angles greater than 40 degrees, RF bandwidths less than 1800 Hz and pulse sequences that do not contain dephasing pulses. Control system 112 may also be configured to utilize a sparse sampling imaging technique without parallel imaging.

In another implementation of magnetic resonance imaging system 100, the main magnet 102 field strength is approximately 0.15 Tesla and control system 112 is configured to utilize gradient field strengths below 10 mT/m, a gradient slew rate above 75 mT/m/ms, flip angles greater than 60 degrees, RF bandwidths less than 1000 Hz and pulse sequences that do not contain dephasing pulses. In this implementation, control system 112 may also be configured to utilize a sparse sampling imaging technique without parallel imaging.

As discussed further herein, certain implementations of the systems, methods and computer software of present disclosure can be beneficial for cine planar, cine multiplanar, or real time volumetric or "4-D" (3-D spatial plus the time dimension) magnetic resonance imaging. Control system 112 may thus be configured to acquire and process data as necessary to reconstruct images to create cine MRI, for example, enabling cine MRI of at least 4 frames per second while maintaining an acceptable specific absorption rate in patient 110.

Conventional wisdom is that a high main magnet field strength is always preferred due to higher signal-to-noise ratio, with the desired field strength being limited mainly by size and cost considerations. Through higher signal-to-noise, contrast, and resolution, a higher field strength typically facilitates an improved ability for physicians to make diagnoses based on the resulting images. Yet, implementations of the present disclosure utilizing low main magnet field strengths (e.g., below 1.0 Tesla) result in high quality images and provide a number of additional benefits.

For example, implementations of the present disclosure can include RF bandwidths less than 1800 Hz, resulting in decreased chemical shift artifacts (i.e., where hydrogen atoms in different chemical environments such as water and fat are partially shielded from the main magnetic field due to the difference in sharing of electrons involved in O—H and C—H chemical bonds, and hence have different nuclear magnetic resonance chemical shifts, appearing in different spatial locations when locating signals with frequency encoding). While high field systems will exhibit significant chemical shift artifacts, and require higher RF bandwidths (and their accompanying lower signal-to-noise ratios), the low field systems disclosed herein can use lower RF bandwidths and maintain high spatial integrity.

In addition, high main magnetic field strength systems will exhibit significant magnetic susceptibility artifacts where the diamagnetic and paramagnetic (and in rare cases ferromagnetic) nature of the imaged subject perturbs the magnetic field, leading to spatially distorted images. Such issues in higher field systems might typically be addressed through an increase in gradient field strengths, but implementations of the present disclosure avoid the same level of artifacts and thus may utilize lower gradient field strengths, resulting in improved signal-to-noise ratio and a lower specific absorption rate.

Moreover, the systems, methods and software discussed herein can be implemented without parallel imaging, which would cause a decrease in the signal-to-noise ratio of the resulting images that would increase with the speed of the imaging. Instead, the sparse sampling techniques disclosed herein allow for high frame rate acquisition with a relatively high signal-to-noise ratio that does not significantly decrease with image acquisition speed, for example, through the use of a priori data acquired before scanning, avoiding the use of "gridded" k-space data, and applying iterative optimization techniques. The use of phased array receive coils may also be avoided in the absence of parallel imaging, thereby achieving high quality imaging with less complex technology. Fewer RF receive channels may be used, in fact, only a single RF receive channel may be employed, along with a less expensive spectrometer.

Certain implementations of the present disclosure can also be employed without surface coils in contact with the patient. Instead, imaging may be performed with merely a body coil integrated into the bore of the MRI that contains both the transmit and receive coils.

In addition, simultaneous multiple slice imaging techniques may be beneficially employed, where multiple imaging slices or sub-volumes may be simultaneously excited and simultaneously read out. One implementation of simultaneous multiple slice excitation can sum multiple RF waveforms with different phase modulation functions resulting in a multiband pulse that can excite desired slices in the presence of a common slice selective gradient.

Furthermore, implementations of the present disclosure may utilize relatively high flip angles, which, at higher main magnet field strengths, would cause excessive patient heating. The higher flip angles in implementations of the present disclosure will result in improved image contrast and signal-to-noise ratios.

Additionally, the low main magnet field strength implementations discussed herein will exhibit faster RF signal decay, allowing for pulse sequences that do not require dephasing pulses (with the attendant advantage of a lower specific absorption rate).

The low main magnet field strength of certain implementations of the present disclosure also allows for lower frequency RF excitation pulses and thus decreased heating of the patient tissues by those pulses.

Further still, the well-controlled specific absorption rates exhibited by implementations of the present disclosure provide the ability to acquire and process data at a speed sufficient for high frame rate cine MRI.

With the numerous above described advantages, implementations of the present disclosure are well-suited for high quality cine MRI having an acceptable patient specific absorption rate. These implementations also control magnetic susceptibility and chemical shift artifacts so as to provide high spatial integrity, which can be critical in certain diagnostic and interventional applications.

Implementations of the present disclosure can be beneficial in numerous applications for diagnostic cine MRI, examples include anatomic localizers, repeated rapid imaging for localization and the study of movement (e.g., phonation), imaging freely moving subjects (e.g., fetal MRI), cardiac imaging, and the like.

Implementations of the present disclosure can also be beneficial in interventional applications, which also benefit from the advantages of high spatial integrity and controlled specific absorption rate. Examples of interventional applications include angioplasty, stent delivery, thrombolysis, aneurysm repair, vertebroplasty, fibroid embolization, and many other applications where fluoroscopy is currently used (and where the use of cine MRI will decrease radiation dose to the patient).

Implementations of the present disclosure may also be used for image guided surgery, and may provide real-time intraprocedural guidance in multiple orthogonal planes, imaging feedback regarding instrument position, guidance and/or warning systems and the like. An open bore MRI implementation, similar to that depicted in FIG. 1 (but with a split RF coil system 106) can be particularly beneficial for such interventional procedures. MRI 100 may thus be configured to allow for surgical intervention in the gap of a split magnet and may further include a robotic surgical device integrated with the system.

Yet another advantage of the low field strength attendant to certain implementations of the present disclosure is the decreased magnetic forces that will be exerted on any interventional equipment employed in conjunction with MRI 100 such as robotic surgery equipment, biopsy instrumentation, cryogenic ablation units, brachytherapy equipment, radiation therapy equipment, and the like.

In one implementation of magnetic resonance imaging system 100, in combination with interventional equipment (e.g., radiation therapy equipment such as a linac), a low field strength, non-superconducting magnet is utilized, for example, a resistive magnet, a permanent magnet, or hybrid magnet.

Another beneficial application of certain implementations of the present disclosure is in the field of image guided radiotherapy. Radiotherapy applications will also benefit from the present disclosure's ability to provide high frame rate cine MRI with high spatial integrity, both of which are key to accurately tracking a target being treated and to avoid hitting patient critical structures with significant amounts of ionizing radiation.

Figure 2:
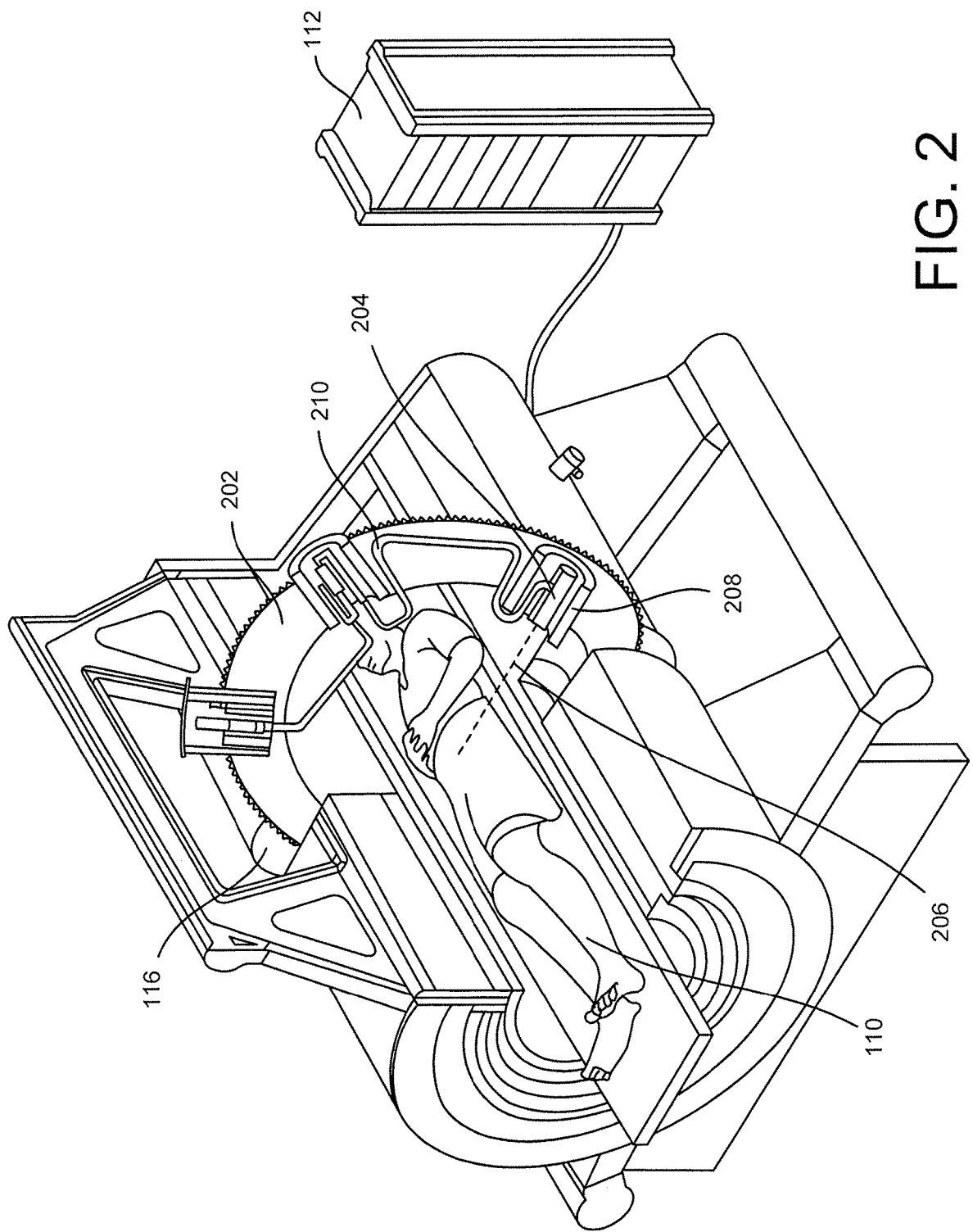
FIG. 2 is a diagram illustrating a simplified perspective view of an exemplary magnetic resonance imaging system incorporating an exemplary interventional device in accordance with certain aspects of the present disclosure.

FIG. 2 illustrates MRI 100 further configured to integrate a radiation therapy device to treat patient 110. In one implementation, MRI 100 may include a gantry 202 positioned in gap 116 of an open bore MRI. Gantry 202 can incorporate radiation therapy device 204, configured to direct a radiation therapy beam 206 toward patient 110. In one particular implementation, radiation therapy device 204 may be a linear accelerator having an energy in the range of 4-6 MV and, as depicted, the components of the linear accelerator may be divided into separate shielding containers 208 spaced about gantry 202. These linac components may then be connected by RF waveguides 210. While FIG. 2 depicts a particular radiation therapy device arrangement, the present disclosure contemplates the integration of any type of radiation therapy system such as proton therapy, heavy ion therapy, radioisotope therapy, etc.

As noted above, control system 112 of magnetic resonance imaging system 100 may be configured for cine MRI and further configured to utilize cine MRI to track the locations of tissues in the human patient 110.

An additional benefit of implementations of the present disclosure utilizing a main magnet 102 with a low field strength is a decrease in distortions of the delivered ionizing radiation dose distribution in patient 110 caused by the magnetic Lorenz force acting on the transport of secondary electrons (and positrons). The Lorenz force exerted by a higher field main magnet would overpower the scattering power of the electrons (and positrons), and cause them to spiral off their natural course, trapping them at low density interfaces—potentially resulting in unintended and harmful dose concentrations in the patient.

Figure 3:
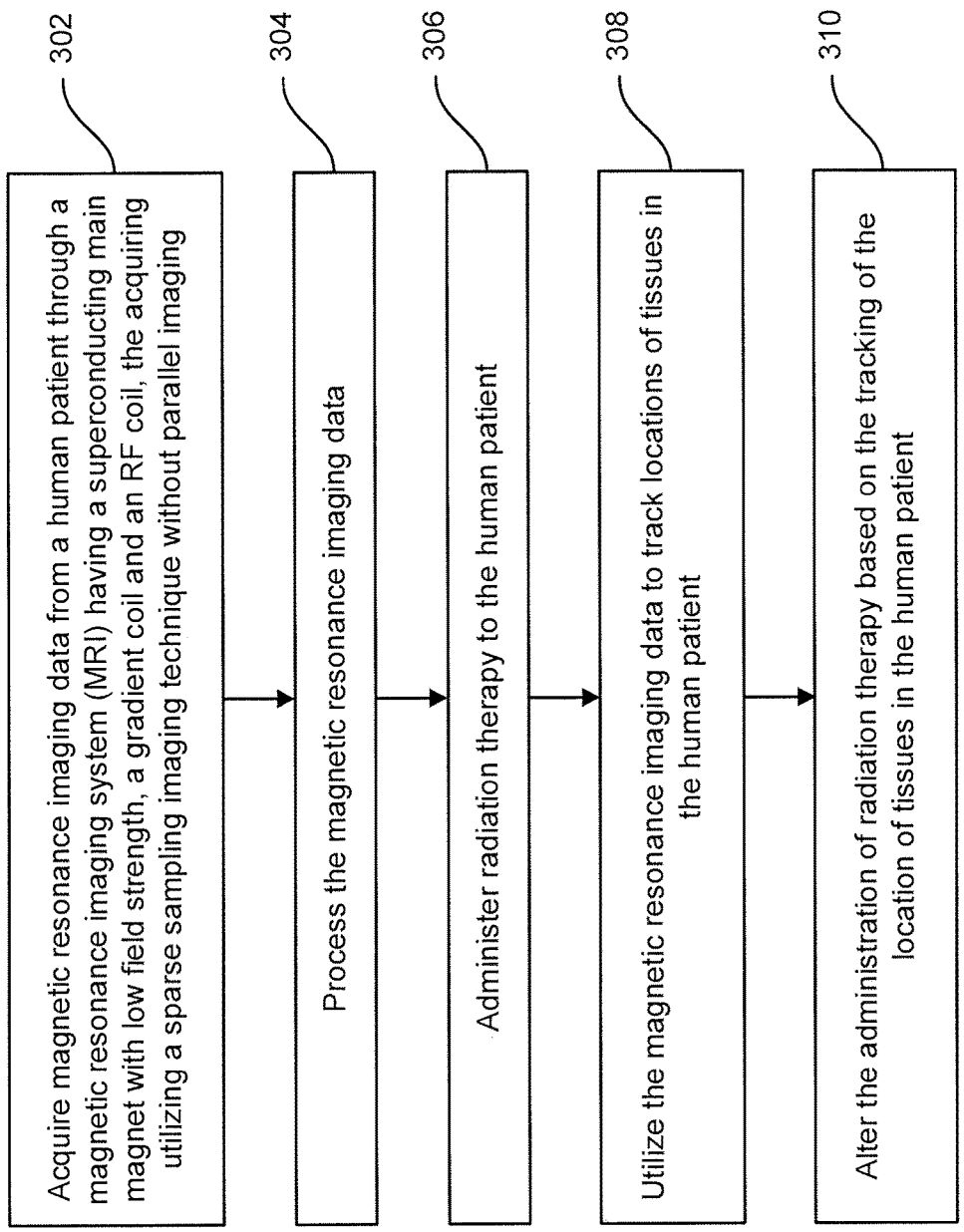
FIG. 3 is a simplified diagram for an exemplary method of real-time MRI-guided radiation therapy in accordance with certain aspects of the present disclosure.

An exemplary method for real-time image guided radiotherapy, consistent with implementations of the present disclosure, is illustrated in FIG. 3. At 302, magnetic resonance imaging data may be acquired from a human patient 110 through magnetic resonance imaging system 100 having a superconducting main magnet with low field strength, a gradient coil assembly 104, and an RF coil system 106, where the acquisition utilizes a sparse sampling imaging technique without parallel imaging. At 304, the magnetic resonance imaging data is processed. At 306, radiation therapy is administered to human patient 110. At 308, the magnetic resonance imaging data is utilized to track the locations of tissue(s) in the patient 110. And, at 310, the administration of radiation therapy may be altered based on the tracking of the location of tissue(s) in patient 110. In altering therapy, actions such as stopping the therapy, reoptimizing the therapy, adjusting the radiation therapy beam and the like are contemplated. The exemplary method illustrated in FIG. 3 may also incorporate any or all of the characteristics described above (e.g., low gradient field strengths, large flip angles, RF bandwidths to maintain spatial integrity, particular pulse sequences, etc.).

When the present disclosure indicates that the magnetic resonance imaging system is configured to operate in a particular manner, it means that such system is setup and intended to be operated in that manner, regardless of whether it may also be configured to utilize pulse sequence(s) or configurations that do not operate in the manner described or claimed herein.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A magnetic resonance imaging system (MRI) comprising:
   a main magnet having a field strength of between 0.1 and 0.5 Tesla;
   a gradient coil assembly;
   an RF coil system; and
   a control system configured for acquisition and processing of magnetic resonance imaging data from a human patient and configured to utilize a sparse sampling imaging technique without parallel imaging; wherein the control system is further configured for an RF bandwidth of less than 1800 Hz.

2. A magnetic resonance imaging system (MRI) comprising:
   a main magnet having a field strength of between 0.1 and 0.5 Tesla;
   a gradient coil assembly;
   an RF coil system; and
   a control system configured for acquisition and processing of magnetic resonance imaging data from a human patient and configured to utilize a sparse sampling imaging technique without parallel imaging; wherein the control system is configured to employ pulse sequences, wherein the pulse sequences do not require dephasing pulses.

3. A computer program product comprising a non-transient, machine-readable medium storing instructions which, when executed by at least one programmable processor, cause the at least one programmable processor to perform operations comprising:
   acquiring, through a control system, magnetic resonance imaging data from a human patient through a magnetic resonance imaging system (MRI) having a main magnet with a field strength of between 0.1 and 0.5 Tesla, a gradient coil assembly and an RF coil system, the acquiring utilizing a sparse sampling imaging technique without parallel imaging; wherein the control system is further configured for an RF bandwidth of less than 1800 Hz; and
   processing the magnetic resonance imaging data, the processing including reconstructing images of the human patient.

4. A computer program product comprising a non-transient, machine-readable medium storing instructions which, when executed by at least one programmable processor, cause the at least one programmable processor to perform operations comprising:
   acquiring magnetic resonance imaging data from a human patient through a magnetic resonance imaging system (MRI) having a main magnet with a field strength of between 0.1 and 0.5 Tesla, a gradient coil assembly and an RF coil system, the acquiring utilizing a sparse sampling imaging technique without parallel imaging; wherein the acquiring employs pulse sequences, wherein the pulse sequences do not require dephasing pulses; and
   processing the magnetic resonance imaging data, the processing including reconstructing images of the human patient.

5. A magnetic resonance imaging system (MRI) comprising:
   a main magnet having a field strength of between 0.1 and 0.5 Tesla;
   a gradient coil assembly; wherein the gradient coil assembly is operable to create a gradient field with gradient field strengths, wherein the gradient field strengths are below 20 mT/m an RF coil system; and
   a control system configured for acquisition and processing of magnetic resonance imaging data from a human patient and configured to utilize a sparse sampling imaging technique without parallel imaging.

6. A magnetic resonance imaging system (MRI) comprising:
   a main magnet having a field strength of between 0.1 and 0.5 Tesla;
   a gradient coil assembly;
   an RF coil system; wherein the RF coil system is operable to create flip angles, wherein the flip angles are greater than 40 degrees; and
   a control system configured for acquisition and processing of magnetic resonance imaging data from a human patient and configured to utilize a sparse sampling imaging technique without parallel imaging.

7. A computer program product comprising a non-transient, machine-readable medium storing instructions which, when executed by at least one programmable processor, cause the at least one programmable processor to perform operations comprising:
   acquiring magnetic resonance imaging data from a human patient through a magnetic resonance imaging system (MRI) having a main magnet with a field strength of between 0.1 and 0.5 Tesla, a gradient coil assembly and an RF coil system, the acquiring utilizing a sparse sampling imaging technique without parallel imaging; wherein the acquiring utilizes gradient field strengths that are below 20 mT/m; and
   processing the magnetic resonance imaging data, the processing including reconstructing images of the human patient.

8. A computer program product comprising a non-transient, machine-readable medium storing instructions which, when executed by at least one programmable processor, cause the at least one programmable processor to perform operations comprising:
   acquiring magnetic resonance imaging data from a human patient through a magnetic resonance imaging system (MRI) having a main magnet with a field strength of between 0.1 and 0.5 Tesla, a gradient coil assembly and an RF coil system, the acquiring utilizing a sparse sampling imaging technique without parallel imaging; wherein the acquiring utilizes flip angles that are greater than 40 degrees; and
   processing the magnetic resonance imaging data, the processing including reconstructing images of the human patient.

* * * * *